United States Patent [19]

Stapersma

[11] Patent Number: 4,873,333
[45] Date of Patent: Oct. 10, 1989

[54] NITROGEN-CONTAINING BIDENTATE COMPOUND IMMOBILIZED ON A SOLID INORGANIC CARRIER

[75] Inventor: Johan Stapersma, Amsterdam, Netherlands

[73] Assignee: Shell Oil Company, Houston, Tex.

[21] Appl. No.: 328,648

[22] Filed: Mar. 27, 1989

Related U.S. Application Data

[62] Division of Ser. No. 165,054, Mar. 7, 1988.

[30] Foreign Application Priority Data

Mar. 25, 1987 [GB] United Kingdom ............... 8707131

[51] Int. Cl.$^4$ ............ C07D 471/04; C07F 7/18; B01J 31/02
[52] U.S. Cl. ............................. 546/14; 546/6; 546/88; 546/256; 546/257; 502/158
[58] Field of Search ............................. 546/14

[56] References Cited

U.S. PATENT DOCUMENTS

| | | | |
|---|---|---|---|
| 3,810,888 | 5/1974 | Chapuriat et al. | 252/240 D |
| 3,886,080 | 5/1975 | Schucker et al. | 252/176 |
| 4,424,359 | 1/1984 | Kaschig et al. | 546/255 |

FOREIGN PATENT DOCUMENTS

| | | | |
|---|---|---|---|
| 1503305 | 3/1978 | United Kingdom | 502/155 |
| 1569346 | 6/1989 | United Kingdom | 502/158 |

OTHER PUBLICATIONS

Rebek Jr. et al., J.A.C.S., 97 (12), 3454 (1975).
Card et al., *Inorganic Chemistry*, 17 (9), 2345 (1978).

*Primary Examiner*—Robert T. Bond

[57] ABSTRACT

The invention relates to nitrogen-containing bidentate compound immobilized on a solid carrier having the formula

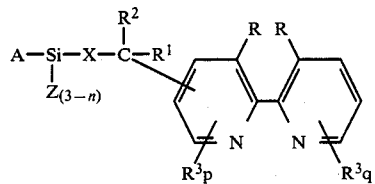

wherein the symbols have specified meanings intermediate thereto and to processes for the preparation.

5 Claims, No Drawings

NITROGEN-CONTAINING BIDENTATE COMPOUND IMMOBILIZED ON A SOLID INORGANIC CARRIER

This is a division of application Ser. No. 165,054 filed Mar. 7, 1988.

BACKGROUND OF THE INVENTION

1. Field of the Invention

The invention relates to a nitrogen-containing bidentate compound immobilized on a solid inorganic carrier, more in particular 2,2'-bipyridine or 1,10-phenanthroline or their derivatives on a solid inorganic carrier, to processes for the preparation of these immobilized products and to intermediate products.

2. State of the Art

It is known that 2,2'-bipyridine and 1,10-phenanthroline may be linked via certain groups to organic polymers, for example, see U.S. Pat. No. 3,810,888; European patent application No. 45.277; *Journal of the American Chemical Society*, 97 (12), 3454 (1975); and *Inorganic Chemistry* 17 (9), 2345 (1978). A disadvantage of these polymers, when used in heterogeneous catalytic reactions, is that they are not generally applicable in the presence of organic solvents, especially polar organic solvents.

There has now been found a group of compounds wherein 2,2-bipyridine, 1,10-phenanthroline or their derivatives are immobilized on a solid inorganic carrier, which compounds are more versatile and are applicable in the presence of organic solvents including polar organic solvents, when used in heterogeneous catalytic reactions. Moreover, the bidentate compounds bound to solid inorganic carriers have a better mechanical and thermal stability than those bound to solid organic polymers.

SUMMARY OF THE INVENTION

The invention provides therefore a nitrogen-containing bidentate compound immobilized on a solid inorganic carrier having the general formula:

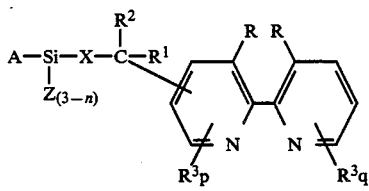

wherein A forms part of a solid inorganic nucleus of an oxide of silicium or of aluminium, Si is silicon, Z is an alkyl, aryl, alkoxy or aryloxy group, n is an integer 1, 2, or 3; and when n is 2 or 3 the remaining Si-bonds are connected with the nucleus A; $R^1$ and $R^2$ independently are hydrogen, an alkyl, or cycloalkyl group of up to 7 carbon atoms or a benzyl group; or both $R^1$ and $R^2$ together form a group $-(CH_2)_a-$ wherein a is an integer of from 2 to 6; each R is hydrogen or both R's together form the group $-CH=CH-$; each $R^3$ individually is an alkyl, phenyl, alkoxy, phenoxy, alkylthio phenylthio group and p and q are integers of from 0 to 2 and of from 0 to 3, respectively; the

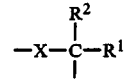

group is linked to a carbon atom of the heterocyclic aromatic ring which occupies the ortho- or para-position with respect to the nitrogen atom in said heterocyclic ring; and $-X-$ is a bivalent organic radical.

The nitrogen-containing bidentate compounds according to the general formula are novel compounds.

The oxides of Si and Al useful in the present invention cannot be simply represented only by $SiO_2$ and $Al_2O_3$, respectively. Instead, such materials usually are hydrates, since they may contain water, which is removed at elevated temperatures, such as by calcination. The surface of the materials contains hydroxyl groups, which react with a silicon compound, which has a bridge function between the inorganic nucleus and the nitrogen containing bidentate compound, The Si-atom of the silicon compound is bound to one oxygen atom of the inorganic nucleus. According to the above general formula said Si-atom may be bound to another oxygen atom of the inorganic nucleus and also to a third oxygen atom of the inorganic nucleus. Schematically it is represented as follows:

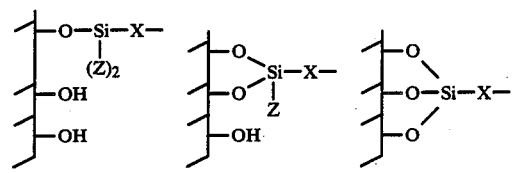

Z represents an alkyl, aryl, alkoxy or aryloxy group of up to 10 carbon atoms, preferably an alkyl or alkoxy group having from 1 to 6 carbon atoms. Preferably the aryl group is a phenyl group.

Any conventional bivalent organic radical can be used for forming bidentate compounds. The bivalent organic radical $-X-$ is preferably a member selected from the class consisting of

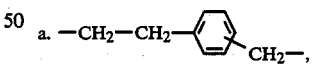

b. $-(CH_2)_m-CH_2-$, wherein m is an interger from 0 to 9, or branched variants thereof,

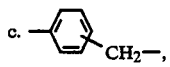

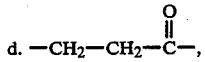

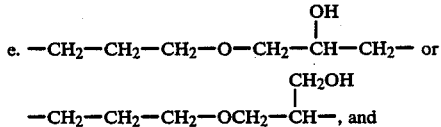

f. 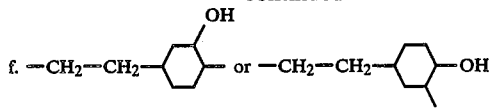

Branched variants are isomers of the group —(CH$_2$)$_m$—CH$_2$— with the same number of carbon atoms.

In the general formula R$^1$ preferably represents hydrogen or an alkyl group of one to six carbon atoms and R$^2$ preferably represents hydrogen or an alkyl group of one to six carbon atoms. R$^1$ and R$^2$ may be the same or different. More preferably R$^1$ is hydrogen and R$^2$ is an alkyl group.

The right part of the general formula contains either a 2,2'-bipyridine skeleton or a 1,10-phenanthroline skeleton, depending whether the R's are both hydrogen or both R's together form the group —CH=CH—. The 2,2'-bipyridine group and the 1,10-phenanthroline group may be substituted by the group R$^3$ in one or both of the rings. When R$^3$ represents alkyl, alkoxy or alkylthio groups the alkyl contains one to six carbon atoms. Preferred are compounds of the general formula wherein p and q are both zero.

The nitrogen-containing bidentate compounds of the general formula may be prepared in two different ways.

A. One process comprises reacting in a first step an oxide of silicium or of aluminium with a compound of the formula

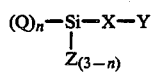

wherein Q is chlorine, bromine, an alkoxy or aryloxy group, Z and n are defined is in the general formula, X is as defined hereinbefore and Y is chlorine, bromine or iodide to obtain a product of the formula

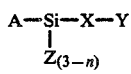

wherein A is defined as in the general formula and Z, n, X and Y are as defined hereinbefore, which latter product is reacted in a second step with a metallated compound of the formula

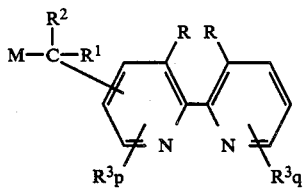

wherein R$^1$, R$^2$ R$^3$, R, p and q are as defined in the general formula, and M is a metal.

B. The second process comprises reacting in a first step a compound of the formula

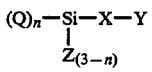

wherein Q is an alkoxy or aryloxy group, Z and n are defined as in the general formula, X is as defined herein-before and Y is chlorine, bromine or iodine, with a metallated compound of the formula

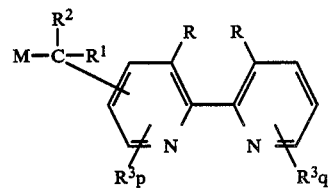

wherein R$^1$, R$^2$, R$^3$, R, p and q are as defined in the general formula, and M is a metal, to an intermediate product of the formula

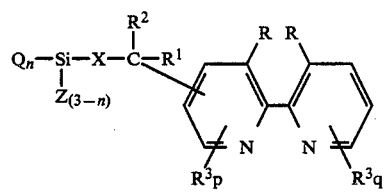

which latter intermediate product in a second step is reacted with an oxide of silicium or aluminum.

Specifically the process comprises reacting in the first step an oxide of silicium or aluminum with a silicon containing organic compound of the group consisting of a. 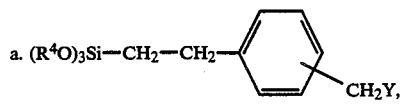

wherein Y is Cl or Br and R$^4$ is an alkyl group of 1 to 4 carbon atoms, b. 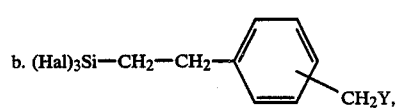

wherein Hal is Cl or Br and Y is Cl or Br, c. (R$^4$O)$_3$Si—(CH$_2$)$_m$—CH$_2$Y, wherein Y is Cl or Br, R$^4$ is an alkyl group of 1 to 4 carbon atoms and m is an integer of from 0 to 9 or branched variants thereof, d. (Hal)$_3$Si—(CH$_2$)$_m$—CH$_2$Y, wherein Y is Cl or Br, Hal is Cl or Br, and m is an integer of from 0 to 9 or branched variants thereof, e. 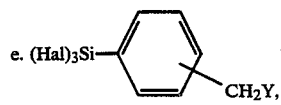

wherein Hal is Cl or Br and Y is Cl or Br, f. 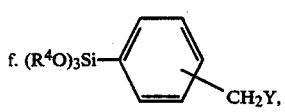

wherein Y is Cl or Br and $R^4$ is an alkyl group of 1 to 4 carbon atoms, and g. 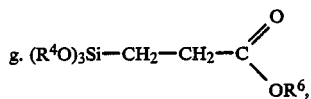

wherein $R^4$ and $R^6$ are alkyl groups of 1 to 4 carbon atoms, and then reacting in a second step with the metallated compound, as defined hereinbefore.

The process further comprises reacting in a first step an oxide of silicium or of aluminium with a silicon containing organic compound of the formula

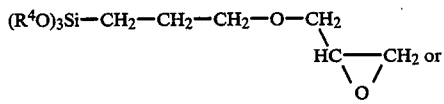

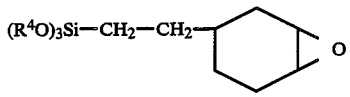

wherein $R^4$ is an alkyl group of 1 to 4 carbon atoms and further reacting in a second step the obtained product with a metallated compound as defined hereinbefore and protonating the reaction product of the second step.

Another process comprises reacting in a first step an oxide of silicium or of aluminium with a silicon containing organic compound of the group consisting of a. 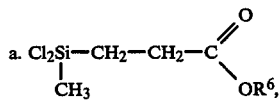

wherein $R^6$ is an alkyl group of 1 to 4 carbon atoms, b. 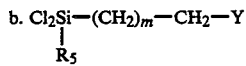

wherein Y is Cl or Br, m is an integer from 0 to 9 and $R^5$ is $C_{1-4}$-alkyl or phenyl, and branched variants thereof, and c. 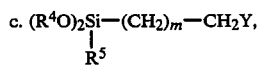

wherein Y is Cl or Br, m is an integer of from 0 to 9, $R^4$ is $C_{1-4}$-alkyl and $R^5$ is $C_{1-4}$-alkyl or phenyl, and branched variants thereof, and then reacting in a second step with the metallated compound.

Another process further comprises reacting in a first step an oxide of silicium or of aluminium with a silicon containing organic compound of the formula

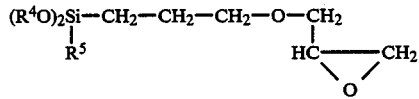

wherein $R^4$ is $C_{1-4}$-alkyl and $R^5$ is $C_{1-4}$-alkyl or phenyl and further reacting in a second step the obtained product with a metallated compound as defined hereinbefore and protonating the reaction product of the second step.

Moreover the process comprises reacting in a first step an oxide of silicium or of aluminium with a silicon containing organic compound of the formula

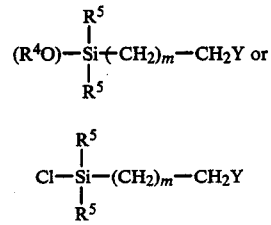

wherein Y is Cl or Br, m is an integer of from 0 to 9, each $R^5$ is a $C_{1-4}$-alkyl or a phenyl group and $R^4$ is a $C_{1-4}$-alkyl group branched variants thereof, and further reacting in a second step the obtained product with the metallated compound.

Also the process comprises reacting in a first step an oxide of silicium or of aluminium with a silicon containing organic compound of the formula

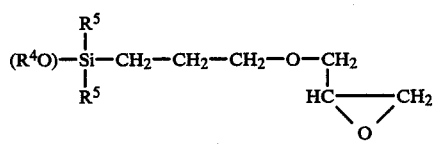

wherein $R^4$ is $C_{1-4}$-alkyl and each $R^5$ is $C_{1-4}$-alkyl or phenyl, and further reacting in a second step the obtained product with a metallated compound as defined hereinbefore, and protonating the reaction product of the second step.

Specifically the process comprises reacting in a first step a silicon containing organic compound of the group consisting of a. 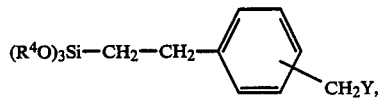

wherein Y is Cl or Br and $R^4$ is an alkyl group of 1 to 4 carbon atoms, b. $(R^4O)_3Si—(CH_2)_m—CH_2Y$, wherein Y is Cl or Br, $R^4$ is an alkyl group of 1 to 4 carbon atoms and m is an integer of from 0 to 9 branched variants thereof, c. 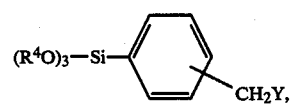

wherein Y is Cl or Br and $R^4$ is an alkyl group of 1 to 4 carbon atoms, and d. 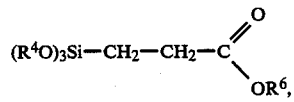

wherein $R^4$ and $R^6$ are alkyl groups of 1 to 4 carbon atoms, with the metallated compound as defined hereinbefore and reacting in a second step the obtained reaction product with an oxide of silicium or of aluminum.

The process further comprises reacting in a first step a silicon containing organic compound of the formula

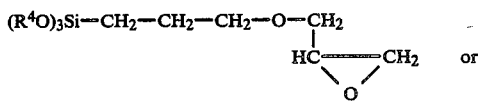

or

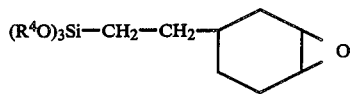

wherein $R^4$ is an alkyl group of 1 to 4 carbon atoms, with a metallated compound as defined hereinbefore, and protonating the reaction product, and reacting in a second step the obtained reaction product with an oxide of silicium or of aluminium.

Another process comprises reacting in a first step a silicon containing organic compound of the formula

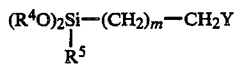

wherein Y is Cl or Br, m is an integer of from 0 to 9, $R^4$ is $C_{1-4}$-alkyl and $R^5$ is $C_{1-4}$-alkyl or phenyl, or branched variants thereof, with the metallated compound as defined hereinbefore and reacting in a second step the obtained reaction product with an oxide of silicium or of aluminium.

Another process further comprises reacting in a first step a silicon containing organic compound of the formula

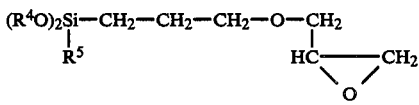

wherein $R^4$ is $C_{1-4}$-alkyl and $R^5$ is $C_{1-4}$-alkyl or phenyl with a metallated compound as defined hereinbefore and protonating the reaction product, and reacting in a second step the obtained reaction product with an oxide of silicium or of aluminium.

Moreover, the process comprises reacting in a first step a silicon containing organic compound of the formula

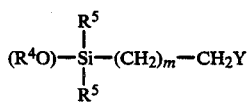

wherein Y is Cl or Br, m is an integer of from 0 to 9, each $R^5$ is a $C_{1-4}$-alkyl or a phenyl group and $R^4$ is a $C_{1-4}$-alkyl group or branched variants thereof with the metallated compound as defined hereinbefore and reacting in a second step the obtained reaction product with an oxide of silicium or of aluminium.

Also the process comprises reacting in a first step a silicon containing organic compound of the formula

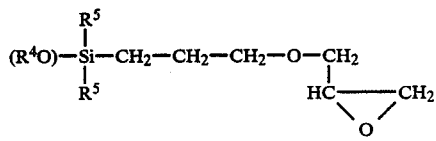

wherein $R^4$ is $C_{1-4}$-alkyl and each $R^5$ is $C_{1-4}$-alkyl or phenyl, with a metallated compound as defined hereinbefore, and protonating the reaction product, and reacting in a second step the obtained reaction product with an oxide of silicium or of aluminium.

The metallated compound as defined hereinbefore preferably contains an alkali metal, more preferably lithium.

The lithiated compound has the formula

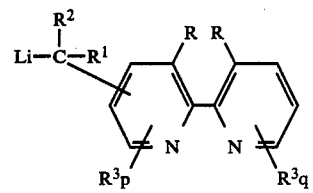

wherein $R^1$, $R^2$, $R^3$, R, p and q are as defined in the general formula and the group

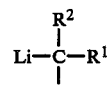

is linked to a carbon atom of the heterocyclic aromatic ring which occupies the ortho- or para-position with respect to the nitrogen atom in said heterocyclic ring.

Preferred compounds, to be used in the metallation of the 2,2'-bipyridine(derivative) or the 1,10-phenanthroline(derivative), are alkali metal amides. An especially preferred metallating compound is lithiumdiisopropylamide. The metallating compound is generally employed in a molar ratio of organometallic compound to 2,2'-bipyridine or 1,10-phenanthroline of about 1 to 1 at a temperature in the range of from $-120°$ C. to $100°$ C., preferably from $-80°$ C. to $30°$ C. The reaction is generally carried out in the presence of an inert solvent, such as diethylether or tetrahydrofuran.

The same temperatures apply when the lithiated 2,2'-bipyridine derivative and the lithiated 1,10-phenanthroline derivative, obtained with the aid of the lithiumdialkylamide, are reacted with the silicon containing organic compounds, exemplified under the embodiments of the process under B (in the first step). The obtained products are hereinafter called "intermediate products".

Temperatures from $20°$ C. to $120°$ C. may be applied when the intermediate products react with the silicium oxide or aluminium oxide nucleus.

Temperatures from $20°$ C. to $120°$ C. may also be applied when the silicium oxide or aluminium oxide nucleus reacts with the silicon containing organic compound, exemplified under the embodiments of the process under A (in the first step).

The invention further relates to an intermediate product of the formula

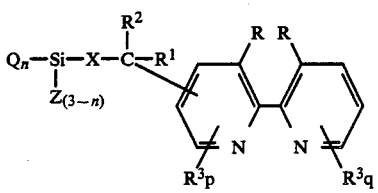

wherein Si is silicon, Q is an alkoxy or aryloxy group of up to 10 carbon atoms; Z is an alkyl, aryl, alkoxy or aryloxy group of up to 10 carbon atoms; n is an integer 1, 2 or 3; $R^1$ and $R^2$ independently are hydrogen, an alkyl or cycloalkyl group of up to 7 carbon atoms or a benzyl group; or both $R^1$ and $R^2$ together form a group —$(CH_2)_a$— wherein a is an integer of from 2 to 6; each R is hydrogen or both R's together form the group —CH=CH—; each $R^3$ individually is an alkyl of 1 to 6 carbon atoms, phenyl, alkoxy of 1 to 6 carbon atoms, phenoxy, alkylthio of 1 to 6 carbon atoms or phenylthio group and p and q are integers of from 0 to 2 and from 0 to 3 respectively; the

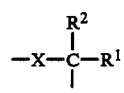

group is linked to a carbon atom of the heterocyclic aromatic ring which occupies the ortho- or para-position with respect to the nitrogen atom in said heterocyclic ring and X is a bivalent organic radical. In this formula the integers p and q are preferably zero, and both R's together preferably form the group —CH=CH—. Preferably $R^1$ is hydrogen and $R^2$ an alkyl group of one to six carbon atoms.

The divalent organic radical —X— is preferably selected from the group consisting

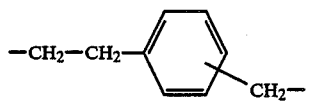

a.

—(CH$_2$)$_m$—CH$_2$—, wherein m is from 0 to 9, b.
or branched variants thereof,

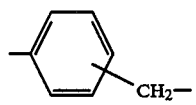

c.

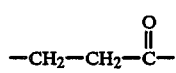

d.

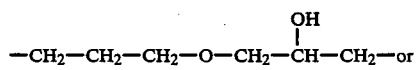

e.

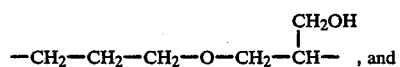

, and

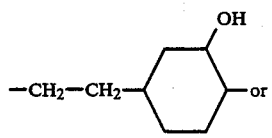

f.

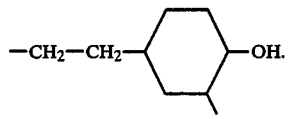

The nitrogen-containing bidentate compounds immobilized on the solid oxide carrier of Si or Al according to the invention will form complexes with the same metal or metal compounds, with which the sole nitrogen-containing bidentates (2,2'-bipyridine and 1,10-phenanthroline) will form complexes.

The nitrogen-containing bidentate compounds immobilized on the solid oxide carrier of Si or Al according to the invention may be advantageously used in many applications, such as extraction and separation processes for metals and for metal compounds or in purification processes. They may be conveniently used in the form of their corresponding complexes with a metal or a metal compound, as a catalyst or catalyst precursor for reactions such as hydrogenation, dehydrogenation, isomerization, hydroformylation, carbonylation and the like.

EXAMPLE 1

2-[(1-Triethoxysilyl)-5-octyl]-1,10-phenanthroline

In a Slenck tube reactor equipped with a magnetic stirrer and in an inert atmosphere (argon) 620 μl 1.5N (1.0 mmol) n-butyllithium solution in n-hexane was added dropwise with the aid of a syringe to a solution of 150 μl di-isopropylamine in 700 μl anhydrous tetrahydrofuran at 0° C. The resulting mixture containing lithium di-isopropylamide was stirred for 15 minutes at 0° C. To this mixture 209.5 mg (0.89 mmol) 2-n-butyl-1,10-phenanthroline (prepared according to T. Kauffmann, J. König and A. Woltermann, Chem. Ber. 109, 3864 (1976)) dissolved in 3 ml anhydrous tetrahydrofuran was added in 5 minutes. The mixture was stirred at 0° C. for 2.75 hours, whereupon 300.5 mg (1.0 mmol) 4-bromobutyl triethoxysilane (prepared from 4-bromo-1-butene according to M. Czakova and M. Capka, J. Mol. Catal., 11, 313 (1981) and A. Kinting, H. Krause and M. Capka, J. Mol. Catal., 33, 215 (1985)) dissolved in 0.5 ml anhydrous tetrahydrofuran was added. The reactor contents were stirred at 0° C. for 17 hours. After this period of time the reactor contents were transferred into a separatory funnel and rapidly equilibrated with 30 ml water and 100 ml diethyl ether. The organic layer was separated, dried over anhydrous magnesium sulphate, and concentrated at 60° C. at reduced pressure (about 20 kPa) using a rotary evaporator. A mixture was obtained of 2-n-butyl-1,10-phenanthroline, 4-bromobutyl triethoxysilane, and 2-[(1-triethoxysilyl)-5-octyl]-1,10-phenanthroline in a ratio of 1:1:1.

EXAMPLE 2A

Mixture of
4-{1-methyl-2-(3-[2-(tri-methoxysilyl)ethyl]phenyl)-ethyl}-1,10-phenanthroline and
4-{1-methyl-2-(4-[2-(trimethoxysilyl)ethyl]phenyl)-ethyl}-1,10-phenanthroline In a Slenck tube reactor equipped with a magnetic stirrer and
in an inert atmosphere (argon) 630 μl 1.5N (1.0 mmol) n-butyllithium solution in n-hexane was added dropwise with the aid of a syringe to a solution of 150 μl diisopropylamine in 700 μl anhydrous tetrahydrofuran at 0° C. The resulting mixture containing lithium di-isopropylamide was stirred for 15 minutes at 0° C. To this mixture 198.8 mg (0.96 mmol) 4-ethyl-1,10-phenanthroline dissolved in 5.5 ml anhydrous tetrahydrofuran was added during 5 minutes. The mixture was stirred at 0° C. for 1.5 hours, whereupon 290.0 mg (1.04 mmol) of a mixture of 1-trimethoxysilyl-2-(4-chloromethyl phenyl)ethane and 1-trimethoxysilyl-2-(3-chloromethyl phenyl)ethane was added with the aid of a syringe. The reactor contents were stirred at 0° C. for 30 minutes and, subsequently, at ambient temperature (18°–22° C.) for 48 hours. The resulting mixture was added dropwise with the aid of a syringe to 130 ml magnetically stirred n-pentane.

The precipitate was isolated by centrifugation and decantantation, and washed with 130 ml n-pentane, and, subsequently, dissolved in 90 ml dichloromethane. The solution was washed rapidly with 50 ml water, dried over anhydrous magnesium sulphate, and concentrated at 60° C. at reduced pressure (ca. 20 kPa) using a rotary evaporator. Residual solvent was removed by a stream of dry nitrogen. Yield: 276.2 mg (0.61 mmol, 64%) yellowbrown oil.

EXAMPLE 2B

Reaction of the mixture of 4-{1-methyl-2-(3-[2-(trimethoxysilyl)-ethyl]phenyl)-ethyl}-1,10-phenanthroline and 4-{1-methyl-2-(4-[2-(trimethoxysilyl)ethyl]phenyl)-ethyl}-1,10-phenanthroline with silica.

In an inert atmosphere 205.5 mg activated silica spheres (1–2 mm; pore volume: 0.93 ml/g; pore diameter: 16 nm; ca. 1.9 mmol silanol groups per gram silica; activated at 150° C. over $P_2O_5$ for 24 hours at less than 1 Pa using a dynamic vacuum) were added to a solution of 247.5 mg (0.55 mmol) of the mixture of 4-{1-methyl-2-(3-[2-(trimethoxysilyl)ethyl]phenyl)-ethyl}-1,10-phenanthroline and 4-{1-methyl-2-(4-[2-(trimethoxysilyl)ethyl]phenyl)-ethyl}-1,10-phenanthroline in 10 ml dry toluene. The resulting mixture was refluxed for 48 hours under argon with slow magnetic stirring. After that period of time 5 ml toluene was distilled off. The residual mixture was cooled to ambient temperature and the functionalized silica spheres were filtered off, purified by sohxlet extraction under argon with dry toluene for 24 hours, and dried over $P_2O_5$ at reduced pressure (ca. 1 Pa) using a dynamic vacuum for 24 hours. Yield: 247.0 mg. Elemental analysis showed a loading of the 1,10-phenanthroline derivative on silica of 0.49 mmol/g unmodified silica.

EXAMPLE 3A

Preparation of silica modified by reaction with 4-bromobutyl triethoxysilane

To an unstirred suspension of 4.97 g activated silica spheres (1–2 mm; pore volume: 0.93 ml/g; pore diameter: 16 nm; ca. 1.9 mmol silanol groups per gram silica; activated at 150° C. over $P_2O_5$ for 24 hours at less than 1 Pa using a dynamic vacuum) in 25.0 ml dry toluene 5.10 g 4-bromobutyl triethoxysilane (prepared from 4-bromo-1-butene according to M. Czakova and M. Capka, *J. Mol. Catal.*, 11, 313 (1981), and A. Kinting, H. Krause, and M. Capka, *J. Mol. Catal.*, 33, 215 (1985)) was added under an inert atmosphere (argon). The resulting mixture was refluxed under argon for 21 hours. After that period of time the reaction mixture was cooled to ambient temperature, and the product was filtered off and washed with dry toluene. Subsequently, 50 ml dry toluene was added to the product under argon, and 10 ml toluene was distilled off. Subsequently, the residual suspension was cooled to ambient temperature, whereupon the product was filtered off, washed with dry toluene, purified by sohxlet extraction with dry toluene for 20 hours under argon, and dried over $P_2O_5$ at reduced pressure (ca. 5 Pa) using a dynamic vacuum for 24 hours. Yield: 5.44 g. Elemental analysis showed a loading of 1-bromobutyl groups on silica of 0.27 mmol/g unmodified silica.

EXAMPLE 3B

Immobilization of 2-n-butyl-1,10-phenanthroline onto silica modified by reaction with 4-bromobutyl triethoxysilane.

In a Slenck tube reactor equipped with a magnetic stirrer and in an inert atmosphere (argon) 670 μl 1.5N (1.0 mmol) n-butyl-lithium solution in n-hexane was added dropwise with the aid of a syringe to a solution of 150 μl diisopropylamine in 700 μl anhydrous tetrahydrofuran at 0° C. The resulting mixture containing lithium di-isopropylamide was stirred for 20 minutes at 0° C., whereupon 202.5 mg (0.86 mmol) 2-n-butyl-1,10-phenanthroline (prepared according to T. Kauffmann, J. König, and A. Woltermann, *Chem. Ber.*, 109, 3864 (1976)) dissolved in 2.0 ml anhydrous tetrahydrofuran was added in 5 minutes. The mixture was stirred at 0° C. for 1.5 hours, and after that period of time 485.0 mg silica spheres, modified by reaction with 4-bromobutyl triethoxysilane were added. The reactor contents were then stirred slowly at ambient temperature for 3 hours, subsequently at 50° C. for 1 hour, and, after that, at ambient temperature for 90 hours, after which period of time 50 μl ethanol was added. The product was filtered off, washed extensively with anhydrous tetrahydrofuran, purified by sohxlet extraction with anhydrous tetrahydrofuran under argon for 24 hours, and dried over $P_2O_5$ at reduced pressure (ca. 5 Pa) for 24 hours using a dynamic vacuum. Yield: 478.4 mg. Elemental analysis showed a loading of 1,10-phenanthroline derivative on silica of 0.29 mmol/g unmodified silica, implying complete reaction of the originally present 1-bromobutyl groups.

EXAMPLE 4A

Preparation of silica modified by reaction with a mixture of 1-trimethoxysilyl-2-(4-chloromethylphenyl)-ethane and 1-trimethoxysilyl-2-(3-chloromethylphenyl)-ethane Modification of 5.02 g activated silica with 4.77 g of a mixture of 1-trimethoxysilyl-2-(4-chloromethylphenyl)-ethane and 1-trimethoxysilyl-2-(3-chloromethylphenyl)-ethane was carried out exactly analogous to the preparation of silica modified with 4-bromobutyl triethoxysilane. Yield: 6.01 g. Elemental analysis showed a loading of (4-) and (3-chloromethylphenyl-)ethyl groups on silica of 0.28 mmol/g unmodified silica.

EXAMPLE 4B

Immobilization of 4-ethyl-1,10-phenanthroline onto silica modified by reaction with a mixture of 1-trimethoxysilyl-2-(4-chloromethylphenyl)-ethane and 1-trimethoxysilyl-2-(3-chloromethylphenyl)-ethane.

In a Slenck tube reactor equipped with a magnetic stirrer and in an inert atmosphere (argon) 670 μl 1.5N (1.0 mmol) n-butyllithium solution in n-hexane was added dropwise with the aid of a syringe to a solution of 150 μl diisopropylamine in 700 μl anhydrous tetrahydrofuran at 0° C. The resulting mixture containing lithium di-isopropylamide was stirred for 20 minutes at 0° C., whereupon 201.3 mg (0.97 mmol) 4-ethyl-1,10-phenanthroline dissolved in 5.0 ml anhydrous tetrahydrofuran was added in 5 minutes. The mixture was stirred at 0° C. for 1.25 hours, and after that period of time 512.1 mg silica spheres, modified by reaction with a mixture of 1-trimethoxysilyl-2-(4-chloromethylphenyl)ethane and 1-trimethoxysilyl-2-(3-chloromethyl-phenyl)ethane, were added. The reactor contents were then heated under argon at 50° C. for 18 hours with slow magnetic stirring, after which period of time 40 μl methanol was added. The mixture was allowed to cool to ambient temperature and the product was filtered off, washed extensively with anhydrous tetrahydrofuran, purified by sohxlet extraction with anhydrous tetrahydrofuran under argon for 24 hours, and dried over $P_2O_5$ at reduced pressure (ca. 5 Pa) for 24 hours using a dynamic vacuum. Yield: 489.2 mg. Elemental analysis showed a loading of 1,10-phenanthroline derivative on silica of 0.24 mmol/g unmodified silica, implying 86% reaction of the originally present chloromethyl groups.

What is claimed is:

1. A compound of the formula:

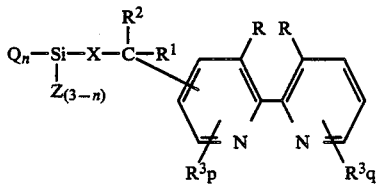

wherein Si is silicon, Q is an alkoxy or aryloxy group of up to 10 carbon atoms; Z is an alkyl, aryl, alkoxy or aryloxy group of up to 10 carbon atoms; n is an integer 1, 2 or 3; $R^1$ and $R^2$ independently are hydrogen, ah alkyl or cycloaklyl of up to 7 carbon atoms or a benzyl group; or both $R^1$ and $R^2$ together form a group —(CH$_2$)$_a$— wherein a is an integer of from 2 to 6; each R is hydrogen or both R's together form the group —CH=CH—; each $R^3$ individually is an alkyl of 1 to 6 carbon atoms, phenyl, alkoxy of 1 to 6 carbon atoms, phenoxy, alkylthio of 1 to 6 carbon atoms or phenylthio group and p and q are integers of from 0 to 2 and from 0 to 3, respectively; the

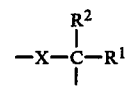

group is linked to a carbon atom of the heterocyclic aromatic ring which occupies the ortho- or para-position with respect to the nitrogen atom in said heterocyclic ring; and X is a bivalent organic radical.

2. A compound according to claim 1, wherein the bivalent organic radical —X— is selected from the group consisting of

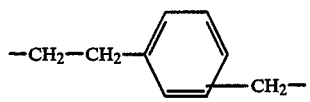 a.

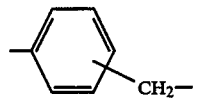, wherein m is from 0 to 9, b.
or branched variants thereof,

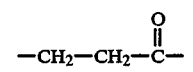 c.

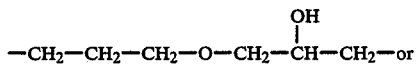 d.

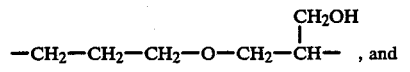 e.

, and

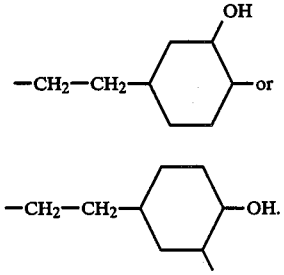 f.

3. A compound according to claim 1 or 2 wherein in the formula the integers p and q are zero.

4. A compound according to claim 1 or 2 wherein in the formula $R^1$ is hydrogen and $R^2$ is an alkyl group of one to six carbon atoms.

5. A compound according to claims 1 or 2, wherein in the formula both R's represent the group —CH=CH—.

* * * * *